(12) United States Patent
Vernickel et al.

(10) Patent No.: US 11,099,249 B2
(45) Date of Patent: Aug. 24, 2021

(54) FEEDING A COIL FOR MAGNETIC RESONANCE IMAGING

(71) Applicant: KONINKLIJKE PHILIPS N.V., Eindhoven (NL)

(72) Inventors: Peter Vernickel, Hamburg (DE); Christoph Leussler, Hamburg (DE); Ingo Schmale, Hamburg (DE); Christian Findeklee, Norderstedt (DE); Oliver Lips, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/754,789

(22) PCT Filed: Sep. 26, 2018

(86) PCT No.: PCT/EP2018/076059
§ 371 (c)(1),
(2) Date: Apr. 9, 2020

(87) PCT Pub. No.: WO2019/072555
PCT Pub. Date: Apr. 18, 2019

(65) Prior Publication Data
US 2020/0309875 A1 Oct. 1, 2020

(30) Foreign Application Priority Data

Oct. 12, 2017 (EP) ..................................... 17196064

(51) Int. Cl.
*G01R 33/34* (2006.01)
*A61B 5/055* (2006.01)
*G01R 33/36* (2006.01)

(52) U.S. Cl.
CPC ........ *G01R 33/34092* (2013.01); *A61B 5/055* (2013.01); *G01R 33/3614* (2013.01); *G01R 33/3621* (2013.01); *G01R 33/3664* (2013.01)

(58) Field of Classification Search
CPC .......... G01R 33/34092; G01R 33/3614; G01R 33/3621; G01R 33/3664; A61B 5/055
See application file for complete search history.

(56) References Cited

U.S. PATENT DOCUMENTS 8,049,504 B2 * 11/2011 Findeklee ............ G01R 33/365
324/322
8,102,177 B2 * 1/2012 McKinnon ......... G01R 33/3415
324/318

(Continued)

OTHER PUBLICATIONS

International Search Report and Written Opinion from PCT/EP2018/076059 dated Jan. 9, 2019.

*Primary Examiner* — Dixomara Vargas

(57) ABSTRACT

The present invention is directed to a system comprising a body coil (9) for magnetic resonance imaging and an RF amplifier connected to the body coil (9) for feeding the body coil (9) with an RF signal, wherein the body coil (9) comprises two different ports (21, 22) for feeding the RF signal into the body coil (9), the body coil (9) is provided with a switch for selectively activating only one single port (21, 22) for feeding the RF signal to the body coil (9) at a time, and the two ports (21, 22) are located at different locations of the body coil (9) such that the dependence of the reflected part of the RF signal fed into the body coil (9) from the weight of the examination object (1) to which the body coil (9) is applied is different for the two ports (21, 22). In this way, a possibility for adapting a MRI measurement to different load situations due to different weights of an examination object (1) in an easy and efficient way is provided, thereby providing the possibility for impedance (Continued)

matching of the body coil by selecting the appropriate driven port.

10 Claims, 2 Drawing Sheets

(56)  References Cited

U.S. PATENT DOCUMENTS

| | | | |
|---|---|---|---|
| 8,717,021 B2* | 5/2014 | Bottomley | G01R 33/58 324/309 |
| 9,107,595 B1* | 8/2015 | Smyth | A61B 5/316 |
| 9,116,214 B2* | 8/2015 | Yang | G01R 33/3664 |
| 9,535,142 B2* | 1/2017 | Leussler | G01R 33/3664 |
| 9,541,614 B2* | 1/2017 | Soutome | G01R 33/34 |
| 9,638,771 B2* | 5/2017 | Soutome | G01R 33/3678 |
| 9,730,643 B2* | 8/2017 | Georgescu | G16H 50/30 |
| 10,185,000 B2* | 1/2019 | Hoile | G01R 33/5659 |
| 10,466,318 B2* | 11/2019 | Zhai | G01R 33/34076 |
| 10,520,564 B2* | 12/2019 | Otake | A61B 5/055 |
| 10,534,049 B2* | 1/2020 | Leussler | A61B 5/055 |
| 10,641,845 B2* | 5/2020 | Otake | G01R 33/3642 |
| 10,705,167 B2* | 7/2020 | Lips | G01R 33/3453 |
| 10,761,158 B2* | 9/2020 | Otake | G01R 33/34076 |
| 10,976,388 B2* | 4/2021 | Yang | A61M 25/09 |
| 2010/0136929 A1* | 6/2010 | Vernickel | G01R 33/34076 455/91 |
| 2010/0244840 A1* | 9/2010 | McKinnon | G01R 33/5612 324/322 |
| 2011/0148411 A1* | 6/2011 | Bottomley | G01R 33/58 324/309 |
| 2013/0234714 A1* | 9/2013 | Li | G01R 33/34092 324/322 |
| 2013/0300415 A1 | 11/2013 | Harvey et al. | |
| 2014/0055136 A1* | 2/2014 | Leussler | G01R 33/3415 324/309 |
| 2014/0139218 A1 | 5/2014 | Findeklee et al. | |
| 2014/0320130 A1 | 10/2014 | Nistler | |
| 2015/0021156 A1 | 1/2015 | Leussler et al. | |
| 2015/0028870 A1 | 1/2015 | Chen et al. | |
| 2015/0054506 A1 | 2/2015 | Eberler et al. | |
| 2015/0177342 A1 | 6/2015 | Lips et al. | |
| 2015/0270719 A1* | 9/2015 | Kurs | H02J 50/40 320/108 |
| 2015/0276897 A1 | 10/2015 | Leussler et al. | |
| 2016/0238677 A1* | 8/2016 | Fischer | G01R 33/36 |
| 2016/0238678 A1 | 8/2016 | Eberler et al. | |
| 2021/0075109 A1* | 3/2021 | Peralta | H01Q 21/28 |

* cited by examiner

FEEDING A COIL FOR MAGNETIC RESONANCE IMAGING

CROSS REFERENCE TO RELATED APPLICATIONS

This application is a U.S. national phase application of International Application No. PCT/EP2018/076059 filed on Sep. 26, 2018, which claims the benefit of EP Application Serial No. 17196064.4 filed on Oct. 12, 2017 and is incorporated herein by reference.

FIELD OF THE INVENTION

The invention relates to the field of feeding a body coil for magnetic resonance imaging (MRI), and in particular to a system comprising a body coil for magnetic resonance imaging and an RF amplifier connected to the body coil for feeding the body coil with an RF signal is provided. The invention further relates to a method for feeding a body coil of a magnetic resonance imaging system with an RF signal by an RF amplifier.

BACKGROUND OF THE INVENTION

As is generally known in the art, in an MRI system, an examination object, usually a examination object, is exposed to a uniform main magnetic field ($B_0$ field) so that the magnetic moments of the nuclei within the examination object form a certain net magnetization of all nuclei parallel to the $B_0$ field, which can be tilted leading to a rotation around the axis of the applied $B_0$ field (Larmor precession). The rate of precession is called Larmor frequency which is dependent on the specific physical characteristics of the involved nuclei, namely their gyromagnetic ratio, and the strength of the applied $B_0$ field. The gyromagnetic ratio is the ratio between the magnetic moment and the spin of a nucleus.

By transmitting an RF excitation pulse ($B_1$ field) which has an orthogonal polarization to the $B_0$ field, generated by means of an RF transmitting antenna or coil, and matching the Larmor frequency of the nuclei of interest, the spins of the nuclei can be excited and brought into phase, and a deflection of their net magnetization from the direction of the $B_0$ field is obtained, so that a transversal component in relation to the longitudinal component of the net magnetization is generated.

After termination of the RF excitation pulse, the relaxation processes of the longitudinal and transversal components of the net magnetization begin, until the net magnetization has returned to its equilibrium state. MR (magnetic resonance) signals which are generated by the precessing magnetization, are detected by means of an RF receiving antenna or coil. The received MR signals which are time-based amplitude signals, are then Fourier transformed to frequency-based MR spectrum signals and processed for generating a MR image of the nuclei of interest within the examination object. In order to obtain a spatial selection of a slice or volume within the examination object and a spatial encoding of the received MR signals emanating from a slice or volume of interest, gradient magnetic fields are superimposed on the $B_0$ field, having the same direction as the $B_0$ field, but having gradients in the orthogonal x-, y- and z-directions. Due to the fact that the Larmor frequency is dependent on the strength of the magnetic field which is imposed on the nuclei, the Larmor frequency of the nuclei accordingly decreases along and with the decreasing gradient (and vice versa) of the total, superimposed $B_0$ field, so that by appropriately tuning the frequency of the transmitted RF excitation pulse (and by accordingly tuning the resonance frequency of the RF/MR receive antenna), and by accordingly controlling the gradient magnetic fields, a selection of nuclei within a slice at a certain location along each gradient in the x-, y- and z-direction, and by this, in total, within a certain voxel of the object can be obtained.

The above described RF (transmitting and/or receiving) antennas can be provided in the form of so-called body coils which can be fixedly mounted within an examination space of an MRI system for imaging a whole examination object, or which are arranged directly on or around a local zone or area to be examined. The invention is about the feeding of such a body coil for MRI with RF excitation pulse ($B_1$ field). As described above, such a body coil is a resonant antenna, designed for generating a well-defined magnetic field inside the human body.

The power fed into a body coil is typically generated by pulsed amplifiers which demand a good or acceptable power matching at their output. 2-channel multi-transmit has become standard for 3T clinical systems in recent years. Typically, the two orthogonal modes of the RF body coil are fed individually by respective RF amplifiers.

The driving ports for the coil modes are matched to increase the power efficiency of the amplifier. However, the body coil impedance, and thus the matching, varies from examination object to examination object and/or imaging position. Conventionally, matching was optimized for a typical load, typically a heavy examination object, accepting inefficient use of RF power in other loading cases.

If a body coil is optimized for a examination object load in an ideal case, only approximately 0.1% of the power is reflected at the body coil port. Taking this configuration when the coil has nearly no loading, up to 30% of the power may be reflected at the ports. To overcome this problem, adaptive methods have been proposed, in which matching is adapted dynamically depending on the coil loading. However, these methods suffer from a more or less complicated matching control circuitry and the need for tuneable high power reactances placed at or very close to the body coil.

In this respect, US 2015/0028870 A1 describes a two-channel magnetic resonance tomography system with a regulation circuit for an amplification system in order to be able to take into account different load situations of the MRI system in a flexible manner. It is thus possible to improve the MRI measurements if the MRI system is set to the respective load situation beforehand by an idle state measurement. The adaptation may also be carried out during the MRI measurement. Therefore, a multiplicity of different load situations may be taken into account by the regulation circuit.

SUMMARY OF THE INVENTION

It is an object of the invention to provide a possibility for adapting a MRI measurement to different load situations due to different weights of an examination object in easy and efficient way.

According to the invention, this object is addressed by the subject matter of the independent claims. Preferred embodiments of the invention are described in the subclaims.

Therefore, according to the invention, a system comprising a body coil for magnetic resonance imaging and an RF amplifier connected to the body coil for feeding the body coil with an RF signal is provided, wherein the body coil comprises two different ports for feeding the RF signal into the body coil, the body coil is provided with a switch for selectively activating only one single port for feeding the RF signal to the body coil at a time, and the two ports are located at different locations of the body coil such that the dependence of the reflected part of the RF signal fed into the body coil from the weight of the examination object to which the body coil is applied is different for the two ports.

In this way, by using one or the other port the impedance of the body coil can be adapted to different loads of the examination object in an easy and reliable way. Depending on the weight and, thus, the load of the examination object, the reflected part of the RF signal fed into the body coil via a given port changes. Therefore, changing from one port to the other port for feeding the RF signal to the body coil may improve the MRI measurement. Hence, the total load range in which the power is efficiently used is increased.

In general, different types of body coils with different shapes and designs can be used for the invention. According to a preferred embodiment of the invention, the body coil comprises two end rings comprised of two circular conductive loops which are connected with each other by a plurality of conductive straight rungs, one port being located at a rung and the other port being located at an end ring. In this respect, if is further preferred that the port which is located at a rung is located at the center of the rung in the middle between the two end rings. Furthermore, the port which is located at an end ring is preferably located at a ring-to-ground connection of the end ring.

Activating only one single port for feeding the RF signal to the body coil may be performed with different types of switches. According to a preferred embodiment of the invention, the switch for selectively activating only one single port for feeding the RF signal to the body coil at a time is comprised of separate lines leading from the RF amplifier to the different ports, respectively, wherein each line comprises a switching diode for opening or closing the connection of the RF amplifier with the body coil, respectively. Such lines and diodes may be integrated into the body coil. However, the switching functionality of the lines may be also integrated into feed cables for the body coil or be part of transmit receive switches of the body coil. Further, the switching diode is preferably arranged between two pieces of lambda/4 cable in the lines. When biased, this deactivates the connected port and, thus, prevents power leakage.

In general, the system may comprise only one single RF amplifier. However, according to a preferred embodiment of the invention, the system comprises a second RF amplifier. Preferably, the second amplifier is connected to the body coil for feeding the body coil with an RF signal comprising a mode which is orthogonal to the mode of the RF signal of the other RF amplifier. In this regard, the RF amplifier is preferably connected to the body coil in the same way as the other RF amplifier but offset by 90° around the central axis of the body coil. In this respect, the preferred embodiments of the invention described above apply in the same way to the part of the system which is related to the second RF amplifier.

It is essential for the invention that, the two ports are located at different locations of the body coil such that the dependence of the reflected part of the RF signal fed into the body coil from the weight of the examination object to which the body coil is applied is different for the two ports. This allows for adapting to different load situations due to different weights of the examination object. This difference of the dependence of the reflected part of the RF signal fed into the body coil from the weight of the examination object to which the body coil is applied can be realized in different ways. According to a preferred embodiment of the invention, the function describing the dependence of the reflected part of the RF signal fed into the body coil from the weight of the examination object to which the body coil is applied for the two ports, respectively, has a single minimum at a specific weight of the examination object, wherein the specific weight of the examination object defined by the minimum of the function is different for the two ports. In this way, the two ports may be related two different preferred load ranges, respectively, i.e. for higher weights and for lower weights of the examination objects, respectively, with a transition point between the ranges in which the respective impedances are the same for both ports.

According to the invention, also a system comprising a body coil for magnetic resonance imaging and an RF receiver connected to the body coil for receiving an RF signal from the body coil is provided, wherein the body coil comprises two different ports for feeding the RF signal to the RF receiver, the body coil is provided with a switch for selectively activating only one single port for feeding the RF signal from the body coil to the receiver at a time, and the two ports are located at different locations of the body coil such that the receiving characteristics of the RF signal is different for the two ports.

While the aspects of the invention addressed further above relate to the transmitter case, this aspect of the invention described here relates to the receiver case. All preferred embodiments of the transmitter case apply for the receiver case in a respective manner.

Preferably, for the receiving characteristics of the RF signal the optimal power transfer from the body coil to the RF receiver and/or ideal noise matching is considered.

Further, according to the invention, a method for feeding a body coil of a magnetic resonance imaging system with an RF signal by an RF amplifier, wherein the body coil comprises two different ports for feeding the RF signal into the body coil, the two ports being located at different locations of the body coil such that the dependence of the reflected part of the RF signal fed into the body coil from the weight of the examination object to which the body coil is applied is different for the two ports, the method comprising the following steps:

selectively activating only one single port for feeding the RF signal to the body coil for a first period of time, determining the reflected part of the RF signal of this port, selectively activating only the other port for feeding the RF signal to the body coil for a second period of time, determining the reflected part of the RF signal of the other port, comparing the amount of the reflected part of the RF signal of the one port and the other port, respectively, and activating the port with the lower amount of the reflected part of the RF signal for performing a MRI measurement.

Preferred embodiments of this method relate to the preferred embodiments of the systems described before.

Finally, the invention also relates to a method for feeding an RF signal from a body coil of a magnetic resonance imaging system to an RF receiver, wherein the body coil comprises two different ports for feeding the RF signal from the body coil to the RF receiver, the two ports being located at different locations of the body coil such that the dependence of the reflected part of the RF signal fed from the body coil from the weight of the examination object to which the body coil is applied is different for the two ports, the method comprising the following steps:

selectively activating only one single port for feeding the RF signal from the body coil to the RF receiver for a first period of time, determining the receiving characteristics of the RF signal reflected part of the RF signal of this port, selectively activating only the other port for feeding the RF signal from the body coil to the RF receiver for a second period of time, determining the receiving characteristics of the RF signal reflected part of the RF signal of the other port, comparing the receiving characteristics of the RF signal amount of the reflected part of the RF signal of the one port and the other port, respectively, and activating the port with the better receiving characteristics of the RF signal for performing a MRI measurement.

This relates to the receiver case for which the same preferred embodiments apply as for the transmitter case described before. The determination of receiving characteristics of the RF signal may be a RF measurement but can also be MR imaging based measurement taking in the order of seconds. The term "better receiving characteristics" refers to at least one predefined measurable value which is characteristic for the receiving of the RF signal and for which the better, i.e. the value with the higher amount can be determined. Examples for such values are power transfer from the body coil to the RF receiver and noise matching quality.

BRIEF DESCRIPTION OF THE DRAWINGS

These and other aspects of the invention will be apparent from and elucidated with reference to the embodiments described hereinafter. Such an embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
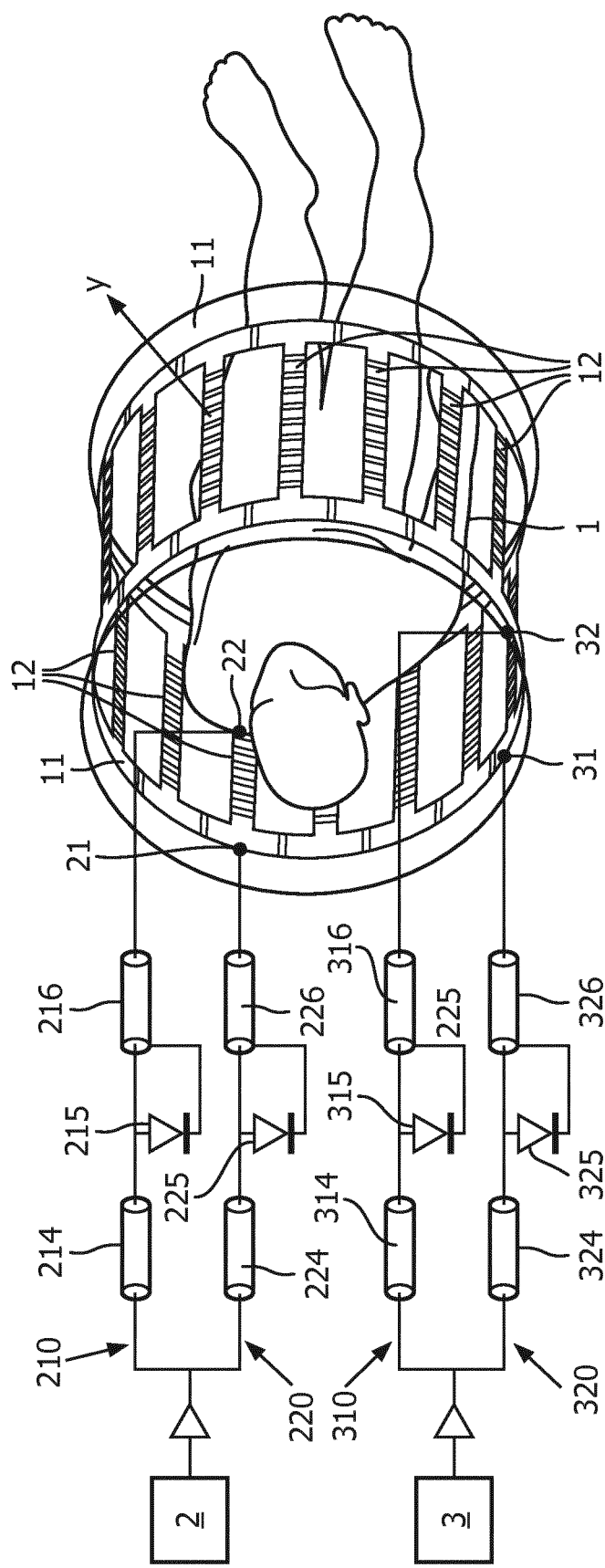
FIG. 1 schematically depicts a system according to a preferred embodiment of the invention.

FIG. 1 depicts a system comprising a body coil 9 for magnetic resonance imaging and two RF amplifiers 2, 3 connected to the body coil 9 for feeding the body coil 9 with two different RF signals, The body coil 9 comprises two different ports 21, 22, and 31, 32 for each RF amplifier 2, 3, respectively, for feeding a respective RF signal into the body coil 9. Further, the body coil 9 is provided with two switches for selectively activating only one single port 21 or 22 for the first RF amplifier 2 and 31 or 32 and the second amplifier 3, respectively, for feeding the RF signal to the body coil 9 at a time.

These switches are comprised of two separate lines 210, 220, 310, 320 leading from the RF amplifiers 2, 3 to the different ports 21, 22, 31, 32, respectively. Each line 210, 220, 310, 320 comprises a switching diode 215, 225, 315, 325 for opening or closing the connection of the RF amplifier 2, 3 with the body coil 9, respectively. The switching diodes 215, 225, 315, 325 are each arranged between two pieces of lambda/4 cable 214, 216, 224, 226, 314, 316, 324, 326. It is to be noted that in FIG. 1 DC supply of the switching diode 215, 225, 315, 325 and RF/DC blocks are not shown for simplicity of the drawing.

The two ports 21, 22, 31, 32 for each RF amplifier 2, 3, respectively, are located at different locations of the body coil 9 such that the dependence of the reflected part of the RF signal fed into the body coil 9 from the weight of the examination object 1 to which the body coil 9 is applied is different for the two ports 21, 22, 31, 32 of each RF amplifier 2, 3, respectively.

The body coil 9 comprises two end rings 11 which are comprised of two circular conductive loops which are connected with each other by a plurality of conductive straight rungs 12, one port 21, 31 of each RF amplifier 2, 3 being located at a rung 12, respectively, and the other port 22, 32 being located at an end ring 11 for each RF amplifier 2, 3, respectively. The ports 21, 31 which are located at one of the rungs 12 are located at the center of the rung 12 in the middle between the two end rings 11. The ports 22, 32 which is located at one of the end rings 12 is located at a ring-to-ground connection of the end ring 11.

It is to be noted that the RF amplifiers 2, 3 reach always drive the same linear modes, even though the feed is being connected at different locations. Only the matching differs for the two feeding locations. One pair of ports 21, 31 may be optimized for strong loading, whereas the other pair of ports 22, 32 may be optimized for weak loading.

The functions describing the dependence of the reflected part of the RF signal fed into the body coil 9 from the weight of the examination object 1 to which the body coil 9 is applied for the two ports 21, 22, 31, 32 of each RF amplifier 2, 3, respectively, has a single minimum at a specific weight of the examination object 1, wherein the specific weight of the examination 1 object defined by the minimum of the function is different for the two ports 21, 22, 31, 32, respectively.

Figure 2B:
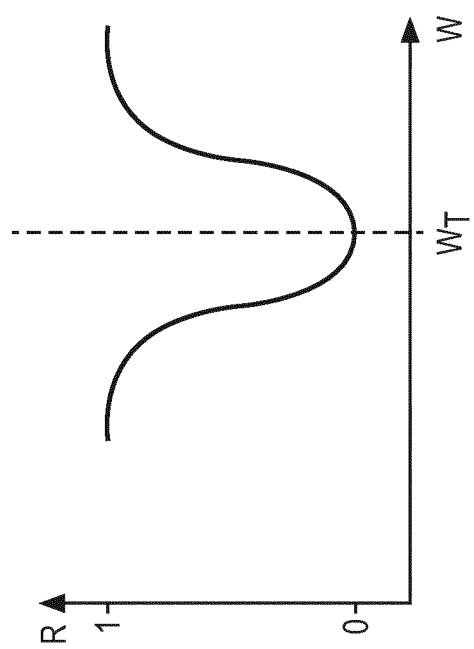
FIG. 2b depicts the function describing the dependence of the reflected part of the RF signal fed into the body coil from the weight of the examination object to which the body coil is applied for the case according to the preferred embodiment of the invention.
Figure 2A:
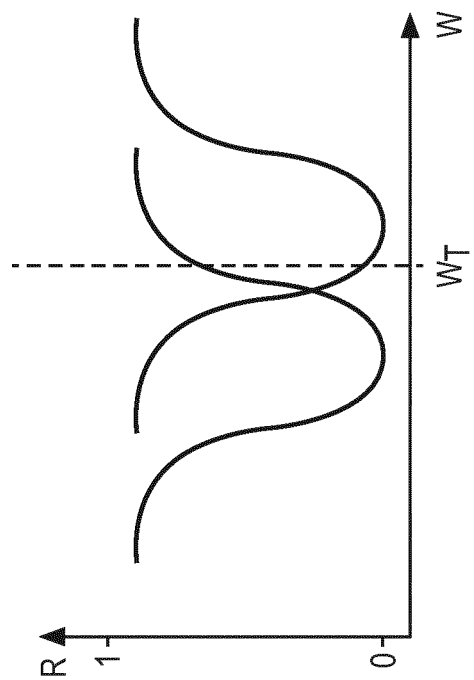
FIG. 2a depicts the function describing the dependence of the reflected part of the RF signal fed into the body coil from the weight of the examination object to which the body coil is applied for a conventional case.

This is shown in FIGS. 2a and 2b wherein FIG. 2a depicts the conventional case with one single port and FIG. 2b depicts the case according to the preferred embodiment of the invention discussed here. The graphs of FIGS. 2a and 2b show the dependence of the ratio R of reflected power to forwarded power from the weight W of the examination object 1 and, thus, the load due to the examination object 1. The vertical dashed line depicts the weight $W_T$ of a typical heavy loading patient as examination object. While in the conventional case, the function is optimized for a typical heavier examination object with weight $W_T$, the design according to the preferred embodiment of the invention provides for a broader range with still acceptable reflected power. This means that still examination objects 1 with typical heavier weight $W_T$ can be measure in an acceptable way while even heavier but also a lot lighter examination objects 1 can be measured with relatively low power reflections. In other words: One port pair 21, 31 has a matching optimized for strong loading, while the other pair of ports 22, 32 is optimized for low loading. Depending on the actual coil loading, either one or the other pair of ports 21, 22, 31, 32 is used while the other one remains unused.

The workflow according to the present embodiment of the invention is as follows: First, the examination object 1, i.e. a patient, is put into an imaging position. Then the shim set to be applied is determined which is a standard routine for MRI imaging. The next step is determining a port matching, which is a quick measurement within ms, and selecting the better matched port pair 21, 31, or 22, 32, respectively. Thereafter a MR sequence is applied for imaging.

This workflow may be part of a normal scan preparation phase where short (milliseconds) RF pulses are consecutively applied to each port 21, 22, 31, 32 and the reflected power at the terminals of the RF amplifiers 2, 3 is measured. A preparation phase software may select the best pair with lowest power reflection.

The port selection may run autonomously, e.g. as part of the RF amplifier functionality. Here, the RF amplifiers 2, 3 continuously tests the individual ports 21, 22, 31, 32 regularly and select the most convenient. An interrupt logic line to the data acquisition system may prevent that testing and selection happens during scanning and in-between scans intended to have identical RF settings.

For asymmetric loading, also a mixed selection of the ports 21, 22, 31, 32 is possible. There may be cases in which the loading of the two coil modes is different. Here it may be reasonable to let one RF amplifier 2 drive at the centre of the rung 12 considering that the first linear mode has low loading. At the same time the other amplifier 3 drives at position considering the heavy loading of the second mode.

The preferred embodiment her is described for the transmitting case (TX). Respective techniques may also be applied for the receiving case (RX). In the RX case the design of the embodiment is the same as depicted in FIG. 1, reference signs 2 and 3 relating then to RF receivers. Optimal pairs of ports 21, 22, 31, 32 for TX and RX are not necessarily the same.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope. Further, for the sake of clearness, not all elements in the drawings may have been supplied with reference signs.

REFERENCE SYMBOL LIST examination object 1
RF amplifier 2
RF amplifier 3
body coil 9
end rings 11
rungs 12
port 21
port 22
port 31
port 32
line 210
lambda/4 cable 214
switching diode 215
lambda/4 cable 216
line 220
lambda/4 cable 224
switching diode 225
lambda/4 cable 226
line 310
lambda/4 cable 314
switching diode 315
lambda/4 cable 316
line 320
lambda/4 cable 324
switching diode 325
lambda/4 cable 326

The invention claimed is:

1. A system comprising:
a body coil for magnetic resonance imaging and an RF amplifier connected to the body coil for feeding the body coil with an RF signal, wherein
the body coil comprises two different ports for feeding the RF signal into the body coil,
the body coil includes a switch for selectively activating only one single port for feeding the RF signal to the body coil at a time, and
the two ports are located at different locations of the body coil such that the dependence of a reflected part of the RF signal fed into the body coil from the weight of the examination object to which the body coil is applied is different for the two ports, and
wherein the two ports are located at said different locations such that a function describing the dependence of the reflected part of the RF signal fed into the body coil from the weight of the examination object to which the body coil is applied for the two ports, respectively, has a single minimum at a predefined specific weight of the examination object, wherein the predefined specific weight of the examination object defined by the minimum of the function is different for the two ports, wherein one predefined specific weight corresponds to a heavy examination object and the other predefined specific weight corresponds to a lighter examination object; and
a measurement unit configured for measuring reflected power of each port at terminals of the RF amplifier.

2. The system according to claim 1, wherein the body coil comprises two end rings comprised of two circular conductive loops which are connected with each other by a plurality of conductive straight rungs, one port being located at a rung and the other port being located at an end ring.

3. The system according to claim 2, wherein the port which is located at a rung is located at the center of the rung in the middle between the two end rings.

4. The system according to claim 2, wherein the port which is located at an end ring is located at a ring-to-ground connection of the end ring.

5. The system according to claim 1, wherein the switch for selectively activating only one single port for feeding the RF signal to the body coil at a time is comprised of separate lines leading from the RF amplifier to the different ports, respectively, wherein each line comprises a switching diode for opening or closing the connection of the RF amplifier with the body coil, respectively.

6. The system according to claim 5, wherein the switching diodes are arranged between two pieces of lambda/4 cable, respectively.

7. The system according to claim 1, wherein the system comprises a second RF amplifier connected to the body coil for feeding the body coil with an RF signal comprising a mode which is orthogonal to the mode of the RF signal of the other RF amplifier, the second RF amplifier being connected to the body coil in the same way as the other RF amplifier but offset by 90° around the central axis of the body coil.

8. A system comprising:
a body coil for magnetic resonance imaging and an RF receiver connected to the body coil for receiving an RF signal from the body coil, wherein
the body coil comprises two different ports for feeding the RF signal to the RF receiver,
the body coil is provided with a switch for selectively activating only one single port for feeding the RF signal from the body coil to the RF receiver at a time, and
the two ports are located at different locations of the body coil such that the two ports are located at different locations of the body coil such that the receiving characteristics of the RF signal is different for the two ports.

9. A method for feeding a body coil of a magnetic resonance imaging system with an RF signal by an RF amplifier, wherein
the body coil comprises two different ports for feeding the RF signal into the body coil, the two ports being located at different locations of the body coil such that the dependence of the reflected part of the RF signal fed into the body coil from the weight of the examination object to which the body coil is applied is different for the two ports and such that such that a function describing the dependence of the reflected part of the RF signal fed into the body coil from the weight of the examination object to which the body coil is applied for the two ports, respectively, has a single minimum at a predefined specific weight of the examination object, wherein the predefined specific weight of the examination object defined by the minimum of the function is different for the two ports, wherein one predefined specific weight corresponds to a heavy examination object and the other predefined specific weight corresponds to a lighter examination object, the method comprises:
selectively activating only one single port for feeding the RF signal to the body coil for a first period of time,
determining the reflected part of the RF signal of this port,
selectively activating only the other port for feeding the RF signal to the body coil for a second period of time,
determining the reflected part of the RF signal of the other port,
comparing the amount of the reflected part of the RF signal of the one port and the other port, respectively, and
activating the port with the lower amount of the reflected part of the RF signal for performing a MRI measurement.

10. A method for feeding an RF signal from a body coil of a magnetic resonance imaging system to an RF receiver, wherein
the body coil comprises two different ports for feeding the RF signal from the body coil to the RF receiver, the two ports being located at different locations of the body coil such that the dependence of the reflected part of the RF signal fed from the body coil (from the weight of the examination object to which the body coil is applied is different for the two ports and such that a function describing the dependence of the reflected part of the RF signal fed into the body coil from the weight of the examination object to which the body coil is applied for the two ports, respectively, has a single minimum at a predefined specific weight of the examination object, wherein the predefined specific weight of the examination object defined by the minimum of the function is different for the two ports, wherein one predefined specific weight corresponds to a heavy examination object and the other predefined specific weight corresponds to a lighter examination object, the method comprises:
selectively activating only one single port for feeding the RF signal from the body coil to the RF receiver for a first period of time,
determining the receiving characteristics of the RF signal of this port,
selectively activating only the other port for feeding the RF signal from the body coil (9) to the RF receiver for a second period of time,
determining the receiving characteristics of the RF signal of the other port,
comparing the receiving characteristics of the RF signal of the one port and the other port, respectively, and
activating the port with the better receiving characteristics of the RF signal for performing a MRI measurement.

* * * * *